United States Patent [19]

Uddén et al.

[11] Patent Number: 4,735,498
[45] Date of Patent: Apr. 5, 1988

[54] EYE MOVEMENT MEASURING APPARATUS

[76] Inventors: Per Uddén, Hofstrasse 1, CH-6064 Kerns, Switzerland; Jan K. Ober, ul. Brzechwy 6, 60-195 Poznan, Poland

[21] Appl. No.: 887,090
[22] PCT Filed: Nov. 18, 1985
[86] PCT No.: PCT/SE85/00467
  § 371 Date: Jul. 16, 1986
  § 102(e) Date: Jul. 16, 1986
[87] PCT Pub. No.: WO86/03113
  PCT Pub. Date: Jun. 5, 1986

[30] Foreign Application Priority Data

Nov. 19, 1984 [SE] Sweden .............................. 8405802

[51] Int. Cl.⁴ .............................................. A61B 3/14
[52] U.S. Cl. ..................................... 351/210; 351/209
[58] Field of Search ...................... 351/209, 210, 246

[56] References Cited

U.S. PATENT DOCUMENTS

| | | | |
|---|---|---|---|
| 2,724,305 | 11/1955 | Brandt | 351/210 |
| 3,450,466 | 6/1969 | Streisinger | 351/246 |
| 3,473,868 | 10/1969 | Young et al. | |
| 3,583,794 | 6/1971 | Newman | |
| 3,594,072 | 7/1971 | Feather | |
| 3,623,799 | 11/1971 | Millodot | |

*Primary Examiner*—John K. Corbin
*Assistant Examiner*—P. M. Dzierzynski
*Attorney, Agent, or Firm*—Oblon, Fisher, Spivak, McClelland & Maier

[57] ABSTRACT

Device for measuring eye movements. At least two radiation sources are located in front of the eyes and at least two radiation detectors are adapted to detect the radiation reflected from the eye, whereby the detectors are located in connection with the radiation sources. In accordance with the invention the radiation sources (3,4) and the detectors (5,6) are disposed in pairs so that one pair is arranged on each side of at least one symmetry plane through the centered eye. The at least two pairs are disposed on a diaphragm (1) which is located at a certain distance from the eye (8) and which is provided with an aperture (2) straight opposite to the eye having a certain form and size thereby to permit the eye to look through the aperture within a certain space angle. A shielding member (7) is disposed aroused the diaphragm and the eye in order to prevent disturbing light from impinging into the eye beyond the light falling through the aperture. Electronic means (11–20) are arranged to detect the radiation which is reflected from the eye and incident against the detector to adjust the radiation from the sources in such a way the radiation intensity detected by each detector will be substantially equal. The difference in the emitted radiation intensity between the two radiation sources is a rough measure of the light reflection from the eye and thus a coarse measurement of the instantaneous position of the eye which together with a fine measurement of the photodetector output forms a high resolution measurement of the eye position.

4 Claims, 1 Drawing Sheet

EYE MOVEMENT MEASURING APPARATUS

BACKGROUND OF THE INVENTION

1. Technical Field

The present invention relates to a device for measuring eye movements, comprising at least two and in front of the eyes located radiation sources and at least two radiation detectors adapted to detect the radiation reflected from the eye and being located in connection with the radiation sources.

2. Background Art

It is previously known to measure eye movements by means of light emitters and light detectors which are placed in front of the eye and are adapted to sense the changing reflection characteristics of each eye due to the different positions, for instance when following a text line or other kind of information which causes the eye to move.

The drawbacks with these known arrangements for measuring eye movements include above all their complexity and the difficulty to adjust them properly and correctly in positions around the eye in order to obtain accurate read-out from the apparatus. Since there is an increasing demand for such apparatus specifically in order to diagnose different degrees of dyslexia among children it should be appreciated that the apparatus hitherto known can only be used under laboratory conditions and require extreme accuracy both from the operator and from the patient in order to obtain useful results. Such apparatus can therefore hardly be used under normal working conditions, for instance in schools or offices since neither of these environments are sufficiently controlled for example as to the illumination from the light sources normally used in such rooms

DISCLOSURE OF THE INVENTION

The main object of the present invention is to provide a measuring device in which the above noted deficiencies of the prior art measuring apparatus have been eliminated. Thus, the invention provides a device which can give extremely accurate measurements and which can be used under normal working conditions, for instance in schools or offices. Moreover, the device according to the invention is far cheaper than any of the prior art measuring apparatus which can only be used in controlled environments as can be obtained in a laboratory.

The object of the invention is realized substantially by the fact that the radiation sources and the detectors are disposed in pairs so that one pair is arranged on each side of at least one symmetry plane through the centered eye, and that the at least two pairs are disposed on a diaphragm which is located a certain distance from the eye and which is provided with an aperture directly opposite to the eye having a certain form and size to thereby permit the eye to look through the aperture within a certain space angle, and that a shielding member is disposed around the diaphragm and the eye in order to prevent disturbing light from impinging into the eye beyond the light falling through the aperature, and that electronic means are arranged to detect the radiation which is reflected from the eye and incident against the detector and to adjust the radiation from the sources in such a way that the radiation intensity detected by each detector will be made substantially equal, whereby the difference in the emitted radiation intensity between the two radiation sources is a rough measure of the light reflection from the eye and thus a coarse measurement of the instantaneous position of the eye which together with a fine measurement of the photodetector output, forms a high resolution measurement of the eye position.

The position of the eye is measured in two steps, first in a coarse measurement, then in a fine measurement. The coarse measurement is carried out when positioning the sensitivity window as close as possible to the actual eye position. The fine measurement is performed within the sensitivity window.

In a suitable embodiment of the invention the arrangement is made in the form of goggles having a device according to the invention for each eye in order to make it possible to study the movements of two eyes simultaneously.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

BEST MODE FOR CARRYING OUT THE INVENTION

Figure 1:
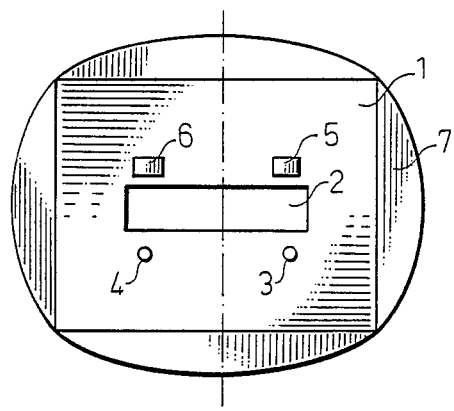
FIG. 1 is a schematical view of a device according to the invention as viewed from the eye.

FIG. 1 shows the device according to the invention in which a diaphragm 1 is provided with an aperture 2 through which the eye can read a text or any other kind of information. Below the aperture there are two IR-illuminators 3 and 4 and above the same there are two photodetectors 5 and 6. The illuminators and the detectors are arranged in pairs wherein one pair is disposed on each side of a symmetry plane through the centered eye, in this embodiment being the vertical plane to the centered eye and dividing the rectangular aperture into two substantially equal portions.

Figure 2:
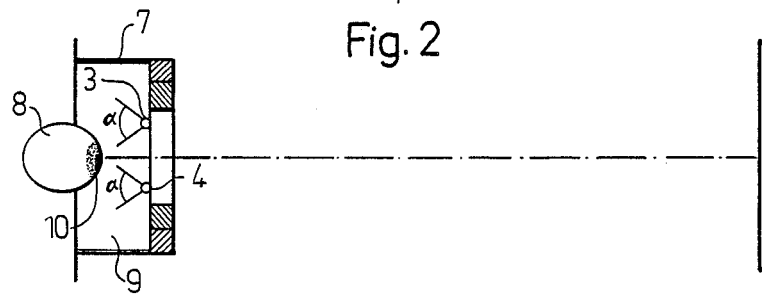
FIG. 2 is a schematical and sectional view of a device according to the invention placed around an eye which observes a text.

As shown in FIG. 2 the two IR-illuminators emit light within a rather wide angle a which can be in the size of about 60°. A shield 7 can be disposed around the diaphragm 1 and also around the eye 8 in order to form a closed space 9 into which no disturbing light can enter from the out-side beyond the light which is incident through the rectangular aperture 2. This means that the reflection from the eye will be diffused and the detectors 5 and 6 will sense this diffused light reflected from that portion of the eye which corresponds to the position of the illuminator 3 or 4. In the figure the eye is shown in centered position with the optical axis passing through the centre of the iris.

Figure 3:
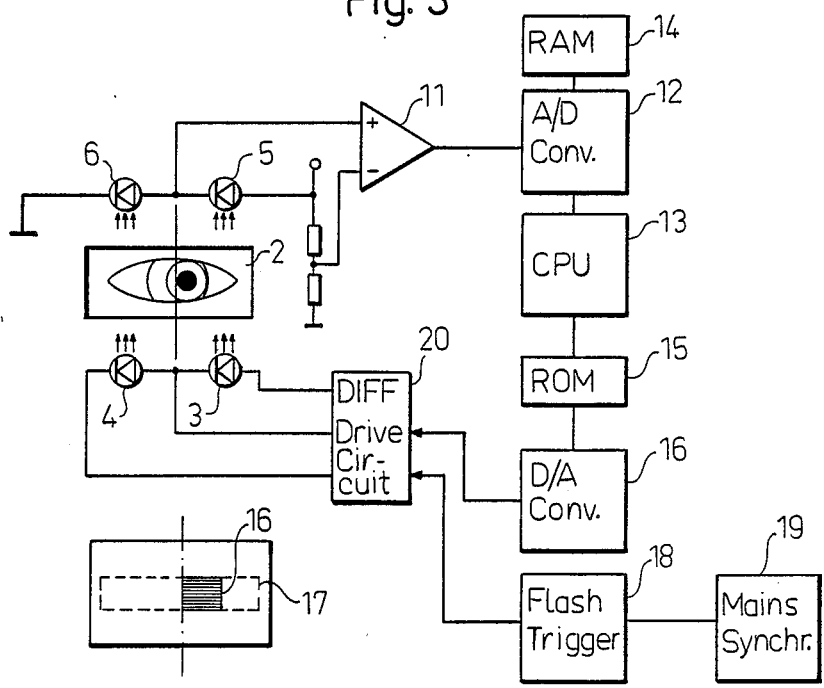
FIG. 3 is an electrical circuit block diagram of a device according to the invention including all the different electrical circuits which are necessary to measure and store the eye movements.

If the eye changes position, as indicated in FIG. 3, the photodetector 5 will receive less reflected light from the eye due to the altered reflection characteristics in the right half of the aperture 2. This will cause an imbalance between the two photodetectors 5 and 6 and result in a certain voltage input to the amplifier 11 which is connected to an analogue-digital converter 12 from which the now digital value of the imbalanced voltage is supplied to a CPU 13 which compares the imbalanced value with the stored values in a ROM 15 and in case this value is above or below the allowed range the CPU 13 establishes how much the illumination from illuminator 3 has to be increased or to be decreased from illuminator 4 in order to re-establish the balance between the two photodetectors 5 and 6. As indicated above the balance between the two detectors 5 and 6 is re-established when the command values are transferred to the illuminators 3, 4 via a digital-analogue converter 16 and a differential drive circuit 20. Moreover, the CPU compares the digital imbalanced value with stored values in a ROM 15 and in case it is within the allowed range, sends it to the RAM as the value representing the eye position within the sensitivity window (fine measure of the eye position). This information is stored in the RAM along with the value sent to the D/A converter (used for correct placement of sensitivity window) as the value representing the coarse position of the eye. Both the rough and fine measure of the eye position stored in the RAM are used to construct the high resolution plot of the eye movement trajectory.

The eye position is measured within the sensitivity window (16) with 8 bits resolution of A/D. As the result of permanent re-establishing of balance by readjusting the illumination, the sensitivity window displaces along the whole dynamic range (17), that is the sensitivity window follows the current position of the eye. The positioning of the sensitivity window is the coarse (rough) measurement of the eye position and is performed with 8 bits resolution of D/A. The fine measurement of the eye position within the sensitivity window is the amplified output from the photodetectors and is carried out with 8 bits resolution of A/D. The possibility to adjust the position of the sensitivity window automatically excludes the necessity of fine placement of measuring its system on the subject head and the correct measurement can be taken without any adjustment at all.

The illuminators 3 and 4 preferably do not emit light constantly but instead in light flashes of a duration of about 0.5 ms for detecting the position of the eye. This has great advantage since the eye can be considered stationary during such a short time period of the flash and moreover, the flash can be synchronized with the mains voltage in order to always obtain the same lighting conditions at the measurement instant. The flash is supplied from a trigger circuit 18 and is synchronized with the mains voltage through a controller 19.

The above embodiment of the invention has been described in connection with a device for measuring eye movements substantially in the horizontal direction but it can of course also be used in a device for measuring both horizontal and vertical movements of the eye. In that case, however, the aperture has to be designed, e.g. in the form of a circular opening which permits detection of horizontal as well as vertical eye movements.

Obviously, numerous modifications and variations of the present invention are possible in light of the above teachings. It is therefore to be understood that within the scope of the appended claims, the invention may be practiced otherwise than as specifically described herein.

We claim:

1. A device for measuring eye movements of the eye of an indvidual, comprising
   a diaphragm;
   at least two radiation sources and at least two radiation detectors located in front of said eye adapted to detect the radiation reflected from the eye and being located in connection with the radiation sources wherein the radiation sources and the detectors are disposed in pairs so that one pair is arranged on each side of at least one symmetry plane through the eye upon being centered, and wherein the at least two pairs are disposed on said diaphragm, said diaphragm being located at a predetermined distance from the eye and which is provided with an aperture directly opposite the eye and having a predetermined form and size to thereby permit the eye to look through the aperture within a predetermined space angle; and
   electronic means for detecting radiation which is reflected from the eye and incident against the detectors and for adjusting the radiation from said radiation sources such that the radiation intensity detected by each detector is substantially equal, whereby the difference in the emitted radiation intensity between the two radiation sources is an approximate measure of the light reflection from the eye and thus a coarse measurement of the instantaneous position of the eye which, together with a fine measurement of the photodetector output, forms a high resolution measurement of the eye position.

2. A device according to claim 1, further comprising a shielding member disposed around the diaphragm and the eye for preventing disturbing light from impinging into the eye beyond the light falling through the aperture.

3. A device according to claim 1, wherein said diaphragm comprises means for restricting the visual field of the eye wherein the form and size of the aperture is determined in accordance with the orientation of the sensitivity axis and the dynamic range of the measuring system, and wherein said detectors are placed on a side of the diaphragm facing the eye and close to the limit of the aperture, thereby avoiding disturbing the visual field, whereby the placement of the gaze of the eye outside the visual field allowed by the diaphragm aperture can be accomplished only by changing the head position so as to require the individuals' head to be turned in such a way that the individual will see the required portion of the visual field, which results in such behaviour that the eye position is constantly kept within the dynamic range of the measuring system defined by the aperture size.

4. A device according to claim 1, wherein said radiation sources comprise means for generating flash eye illumination for measurement of eye position so as to render the eye stationary during measurement and which includes means for triggering the flash synchroneously with external light fluctuations so as to allow recording of eye movement under standard lighting conditions.

* * * * *